United States Patent [19]

Sakai et al.

[11] 4,444,040
[45] Apr. 24, 1984

[54] METHOD AND APPARATUS FOR DETECTING GAS COMPONENTS IN OIL IN OIL-FILLED DEVICE

[75] Inventors: Seiichi Sakai, Kagawa; Toshihiko Gange, Takamatsu; Katuo Sugawara, Hitachi; Hideo Tsukioka, Mito; Ictitaro Tani, Kitaibaraki; Shigeo Shiono; Etsunori Mori, both of Hitachi, all of Japan

[73] Assignees: Hitachi, Ltd.; Shikoku Electric Power Company, Inc., both of Tokyo, Japan

[21] Appl. No.: 400,020

[22] Filed: Jul. 20, 1982

[30] Foreign Application Priority Data

Jul. 27, 1981 [JP] Japan ................. 56-117925
Jul. 27, 1981 [JP] Japan ................. 56-117926

[51] Int. Cl.³ .......................................... G01N 7/10
[52] U.S. Cl. ............................................. 73/19
[58] Field of Search .................. 73/19, 23.1, 863.23

[56] References Cited

U.S. PATENT DOCUMENTS 3,405,551 10/1968 Halasz ................. 73/23.1
4,112,737 9/1978 Morgan .................... 73/19
4,236,404 12/1980 Ketchum et al. ........... 73/23.1
4,402,211 9/1983 Sugawara et al. ............ 73/19

FOREIGN PATENT DOCUMENTS 807140 2/1981 U.S.S.R. .................. 73/19

Primary Examiner—Stephen A. Kreitman
Attorney, Agent, or Firm—Antonelli, Terry & Wands

[57] ABSTRACT

In an apparatus for detecting gas components in the oil in an oil-filled device, which comprises a gas-storing chamber being provided at an oil-filled device containing an insulating oil through a gas-permeating material capable of separating gas components from the insulating oil, a gas calibration tube being provided at the gas-storing chamber through a switch valve, and a gas chromatographic device connected to the gas calibration tube through the switch valve, any influence of gas components in a subatmospheric pressure is eliminated and exact concentrations of gas components are detected by providing at least one stirring mixer having at least one throttle perforation in a carrier gas passage for supplying the gas components from the gas calibration tube to the gas chromatographic device at the upstream side of a gas separation column of the gas chromatographic device, or by proving a circulation passage between the gas-storing chamber and the gas calibration tube, a valve capable of being exposed to the atmosphere at the circulation passage, and a gas circulation unit at the circulation passage for circulating the gas in the circulation passage.

6 Claims, 5 Drawing Figures

METHOD AND APPARATUS FOR DETECTING GAS COMPONENTS IN OIL IN OIL-FILLED DEVICE

BACKGROUND OF THE INVENTION

1. Field of the Invention

This invention relates to a method and an apparatus for detecting gas components in the oil in an oil-filled device, and particularly to a method and an apparatus for detecting gas components in the oil in an oil-filled device, which are suitable for separating and detecting dissolved gas components in a degasified insulating oil in the oil-filled device to find an abnormality of the device.

2. Description of the Prior Art

It is well known that when an abnormality such as local overheating or partial discharging occurs in an oil-filled electric device such as transformer, rectifier, capacitor, cable, etc., the insulating oil or solid insulated article is decomposed to produce the gases of $H_2$ and hydrocarbon types such as $CH_4$, $C_2H_2$, $C_2H_4$, $C_2H_6$, etc., and/or gases of other type such as $CO$, $CO_2$, etc., and most of these gases stady dissolved in the insulating oil. Therefore, if the gases dissolved in the insulating oil in an oil-filled electric device are constantly monitored, it is possible to detect abnormality in said device in its early stage.

Some of the present inventors proposed to detect gas components dissolved in the insulating oil in an oil-filled device, where the dissolved gas components are separated from the insulating oil in an oil-filled device, the separated gas components are stored in a gas storing chamber, or in a gas calibration tube connected to the gas storing chamber, and the stored gas components are led to a gas separation column from the gas storing chamber or the gas calibration tube to detect the gas components by a gas detector (Japanese Laid-open Patent Application No. 56-162049, U.S. patent application Ser. No. 265,656 now U.S. Pat. No. 4,402,211).

However, when the dissolved gas components are detected by the gas detector in combination with a device for separating gas components from an insulating oil through a gas-permeating material, and when a degasified oil is used as the insulating oil for an oil-filled device, for example, in a transformer, a subatmospheric pressure prevails in the gas storing chamber or in the gas calibration tube, because the gas components in the gas storing chamber or in the gas calibration tube permeate in a reversed direction through the gas-permeating material from the gas-storing chamber into the degasified insulating oil, and absorbed therein owing to the principle of equilibrium. The subatmospheric pressure is thus a problem. That is, in the detection of gas components it is not advantageous from the viewpoint of cost to quantitatively determine the respective gas components by way of integrated output values, and it is the ordinary expedient to make quantitative determination by way of peak output values. However, if a subatmospheric pressure prevails in the gas-storing chamber or in the gas calibration tube in the quantitative determination of the respective gas components by way of peak output values by gas chromatography, the peak output values tend to be larger under the subatmospheric pressure than under the normal pressure. That is, correct peak output values cannot be measured. This is because the peak output values of the respective gas components increase in proportion to the degree of subatmospheric pressure prevailing in the gas-storing chamber or in the gas calibration tube. As shown in FIG. 1, such relations are observed for $H_2$, $CO$ and $CH_4$ gas components dissolved in insulating oil that the peak output values in mV are increased in proportion to the degree of subatmospheric pressure in a gas-storing chamber or in a gas calibration tube.

Particularly in the case of detecting gas components having a short gas chromatographic detection time, the peak output values are greatly influenced by the degree of subatmospheric pressure. In the detection of permeated gas components, the permeated gas components are pushed off from the gas calibration tube by a carrier gas and without substantial diffusion of the permeated gas components into the carrier gas due to a very short time, the pushed gas enters into the gas chromatographic device as a zone under a subatmospheric pressure, giving the influence of the subatmospheric pressure to the peak output values. Thus, it has been necessary in the quantitative determination of permeated gas components to measure the pressure prevailing in a gas-storing chamber or in a gas calibration tube to make the necessary correction of pressure. However, this will not only complicate the measuring operation, but also requires additional special devices such as a pressure gage, etc.

The degasified insulating oil usually still contains about 0.5 to about 2.0% of gas components, and thus a subatmospheric pressure prevails in the gas-storing chamber or in the gas calibration tube in terms of a pressure ratio of about 0.05 to 0.1 to the normal pressure as unity. Thus, a subatmospheric pressure prevailing in the gas-storing chamber or in the gas calibration tube has been a problem.

SUMMARY OF THE INVENTION

An object of the present invention is to provide a method and an apparatus for detecting gas components in an oil-filled device, which can exactly determine a gas concentration with a high reliability, even if a subatmospheric pressure prevails in a gas-storing chamber or in a gas calibration tube.

To attain the said object, the present invention provides an apparatus for detecting gas components in an oil-filled device, which comprises a gas-storing chamber provided at an oil-filling device through a gas-permeating material capable of separating gas components from an insulating oil, a gas calibration tube connected to the gas-storing chamber through a switch valve, and a gas chromatographic device for measuring gas components, the device being connected to the gas calibration tube, wherein a stirring mixer having a throttle perforation is provided in a carrier gas passage for conveying the gas components from the gas calibration tube to a gas separation column of the gas chromatographic device at the upstream side of the gas separation column, and the gas components under a subatmospheric pressure are mixed together by contraction and expansion through the stirring mixer before entering into the gas separation column, thereby preventing increases in peak output values under the subatmospheric pressure.

Furthermore, the present invention provides a method for detecting gas components in an oil-filled device which comprises leading air to a gas-storing chamber and a gas calibration tube connected to the gas-storing chamber before quantitative determination of gas components, thereby bringing the gas components into the normal pressure, uniformly mixing the gas in the gas-storing chamber and the gas calibration tube, and then supplying the gas to a gas chromatographic device as another means of eliminating the influence of the permeated gas component under a subatmospheric pressure, and also provides an apparatus for carrying out the method, which comprises a circulating passage being provided between a gas-storing chamber and a gas calibration tube, a valve capable of exposing the circulating passage to open atmosphere being provided in the circulating passage, and a gas circulating device for circulating the gas in the circulating passage. According to the foregoing structure, the gas under a subatmospheric pressure is elevated to the normal pressure, while circulating the gas, thereby making the concentration of gas components uniform, and preventing any increase in peak output values under a subatmospheric pressure to assure exact measurement of gas components.

The present invention will be described in detail below on the basis of embodiments, referring to the drawings.

DETAILED DESCRIPTION OF THE INVENTION

Figure 2:
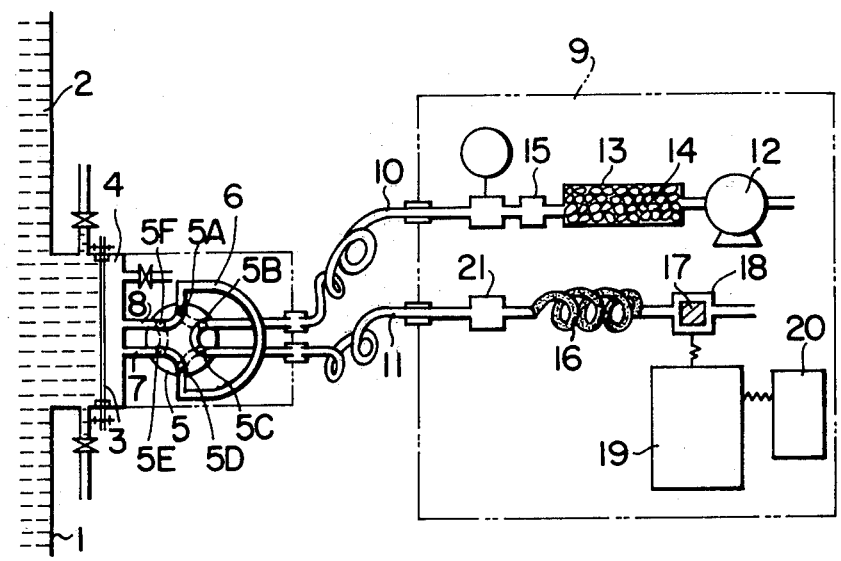
FIG. 2 is a cross-sectional view of an apparatus for detecting gas components in the oil in an oil-filled device according to one embodiment of the present invention.

In FIG. 2, an insulating oil 2 is filled in a transformer casing 1, and a gas permeating material 3 capable of permeating only gas components from the insulating oil 2 while inhibiting permeation of oil is provided at the side wall of the casing 1 and in contact with the insulating oil 2. A gas-storing chamber 4 is provided at the side wall of casing 1 through the gas-permeating material 3.

On the other hand, a circular, 6-way switch valve 5 is provided at the outside of casing 1, and 6 ports 5A–5F of switch valve 5 are provided at equal angles at the circumference of the switch valve. A gas calibration tube 6 is provided to connect a pair of ports 5A and 5D positioned at 180°. A pair of adjacent ports 5E and 5F of the switch valve are connected to communication pipes 7 and 8, respectively, which are open to the gas-storing chamber 4. Another pair of ports 5B and 5C are connected to a carrier gas introducing pipe 10 and a discharge pipe 11, respectively, which are connected to a gas chromatographic device 9 for measuring gas components in the gas calibration tube 6. Thus, the gas calibration tube 6 can be connected either to the gas-storing chamber 4 or to the gas chromatographic device 9.

On the other hand, the gas chromatographic device 9 has an air supply unit 12 for supplying air as a carrier gas to the pipe 10. Air is introduced into the pipe 10 from the supply unit 12 through a drier unit 14 filled with a drying agent 13 and a flow rate controller 15. Furthermore, the gas chromatographic device 9 has a gas separation column 16 connected to the carrier gas discharge pipe 11, and a unit 18 containing a gas sensor 17. The gas sensor is connected to a gas sensor power source 19, which is connected to a recoder 20.

In the normal state, port 5F of switch valve 5 is connected to port 5A, and port 5D to 5E so that the gas-storing chamber 4 may be communicated with the gas calibration tube 6. Thus, the gas-storing chamber 4 and the gas calibration tube 6 form a circulation passage together with the communication pipes 7 and 8 connected thereto.

In the normal state, the carrier gas from the gas chromatographic device 9 is by-passed, because ports 5B and 5C of switch valve 5 are communicated with each other.

Figure 3:
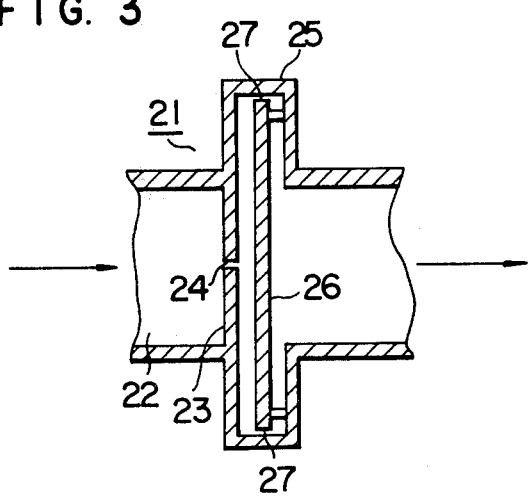
FIG. 3 is a cross-sectional view of a stirring mixer according to one embodiment of the present invention.

In the gas chromatographic device 9 of such a structure, a stirring mixer 21 is provided in the carrier gas discharge pipe 11 at the upstream side of the gas separation column 16. Detailed structure of stirring mixer 21 is shown in FIG. 3. The stirring mixer 21 has a gas contraction plate 23 as if it chokes the carrier gas passage 22. The gas contraction plate 23 is an orifice plate having at least one throttle perforation 24 at the center of the passage 22. The throttle perforation has a considerably smaller area than the cross-sectional area of the passage 22. In the downstream zone just after the gas contraction plate 23, an expansion section 25 having a larger area than the cross-sectional area of the passage 22 is provided. In the expansion section 25, a gas impingement plate 26 is provided to face the gas contraction plate 23 at a predetermined distance. The gas impingement plate 26 is a blind plate with a small clearance 27 between the peripheral end of the plate 26 and the inner peripheral wall of the expansion section 25. Thus, the gas, as introduced into the passage 22, is contracted through the throttle perforation 24 and radially expanded by the gas impingement plate 26. Then, the gass passes through the clearance 27 to the gas separation column 16.

The apparatus for detecting gas components in the oil of such a structure works as follows.

When degasified insulating oil 2 is filled in the transformer, a subatmospheric pressure prevails in the gas-storing chamber 4 and the gas calibration tube 6 connected thereto. When the 6-way valve 5 is switched in that state, the gas calibration tube 6 is connected to the pipes 10 and 11. When a carrier gas is supplied to the pipe 10 from the air supply unit 12, the gas in the gas calibration tube 6 is pushed off from the tube 6 by the carrier gas and is led to the stirring mixer 21 as a zone of subatmospheric pressure through the tube 11.

In the stirring mixer 21, the gas is contracted through the throttle perforation 24, whereby the gas flow speed is suddenly accelerated. Then, the gas hits the gas impingement plate 26 provided in the expansion section of large space at a high speed. Thus, the gas is contracted through the throttle perforation 24 and then expanded, and thus stirred and mixed by the gas impingement plate 26. Then, the gas is led to the gas separation column 16 through the clearance 27 at the peripheral end of the impingement plate 26. The gas components are measured under the reduced influence of the subatmospheric pressure.

Figure 1:
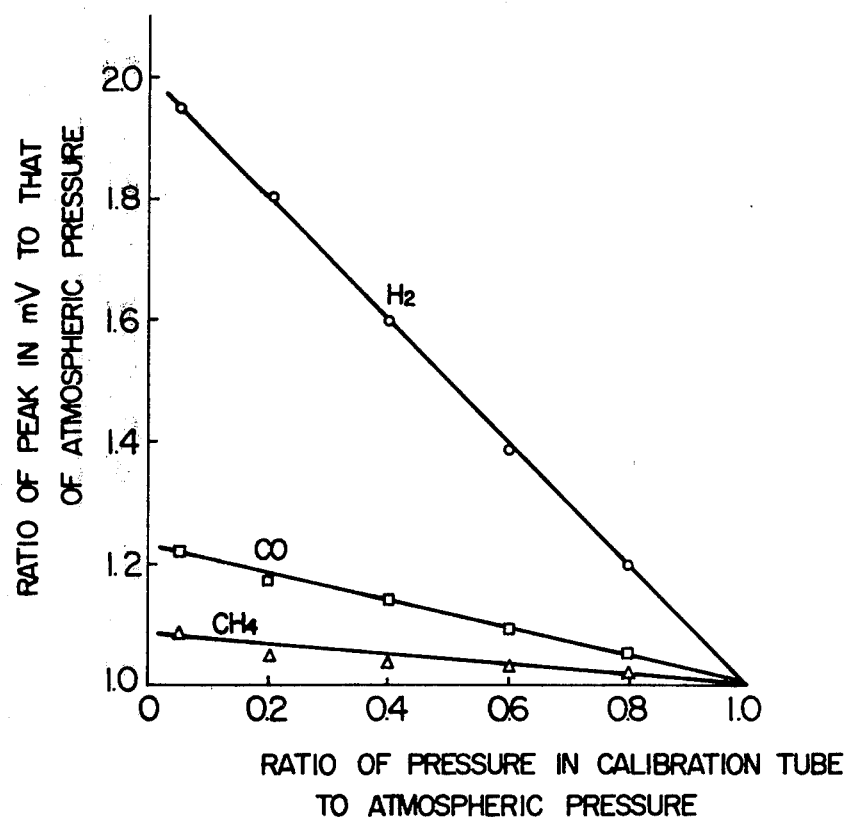
FIG. 1 is a diagram showing relations between a pressure ratio in a gas calibration tube to the normal pressure as unity and the peak output ratio to that under the normal atmosphere as unity according to the conventional art.
Figure 4:
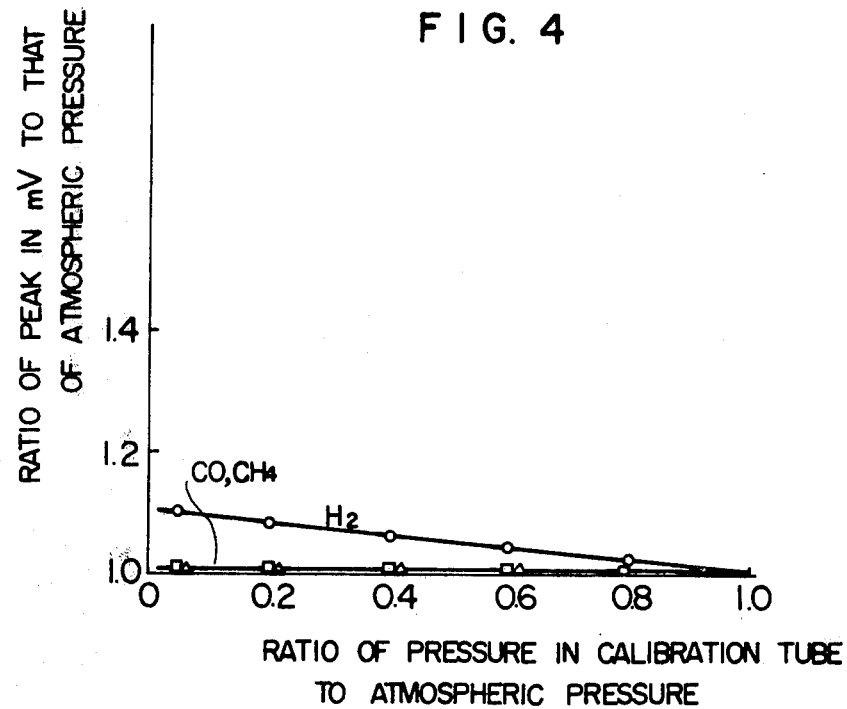
FIG. 4 is a diagram showing relations between a pressure ratio in a gas calibration tube to the normal pressure as unity and a peak output ratio to that under the normal pressure as unity according to one embodiment of the present invention.

FIG. 4 shows relations between ratios of pressure in the gas calibration tube 6 to the normal pressure as unity and ratios of peak output value in mV to that under the normal atmosphere as unity for gas components of $H_2$, CO, and $CH_4$ as obtained on gas chromatogram, which corresponds to FIG. 1.

The gas calibration tube 6 has a volume of 10 ml, and the gas separation column 16 has a length of 1 m, where activated carbon is used as a column filler. The gas sensor 17 is of catalytic combustion type. These conditions are equal in both FIG. 1 and FIG. 4.

As is obvious from FIG. 4, the ratios of the first peak output values for $H_2$ is much less influenced by the subatmospheric pressure in the gas calibration tube 6, and an increase in the peak output values under the subatmospheric pressure can be effectively suppressed.

An embodiment of stirring mixer 21 is shown in FIG. 3, and the stirring mixer is not limited to such structure. That is, various other structures can be used, so long as satisfactory stirring-mixing can be attained.

The number of stirring mixer 21 is not limited to 1, and a better effect can be obtained by at least two stirring mixers in series. Various types of stirring mixer can be used in various combinations. The switch valve 5 is not limited to the embodiment shown in FIG. 2, so long as it works similarly.

As described above, changes in the peak output values on the gas chromatogram can be suppressed to minimum even if the pressure in the gas calibration tube is changed, and thus correction of pressure in the gas calibration tube is not required for each measurement. The gas concentration can be exactly and effectively determined with less measuring operations.

Figure 5:
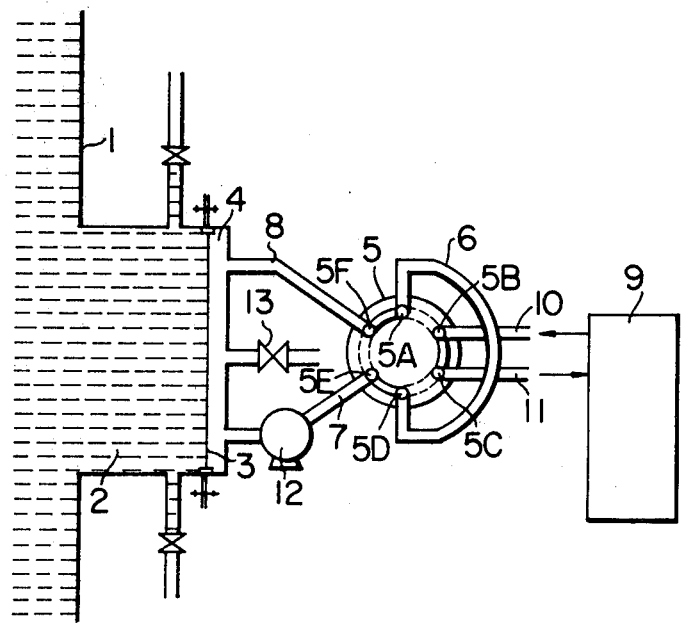
FIG. 5 is a cross-sectional view of an apparatus for detecting gas components in the oil in an oil-filled device according to another embodiment of the present invention

In FIG. 5 another embodiment of the present invention is shown, where the same members as in FIG. 2 are identified with the same reference numerals.

In the circulation passage comprising the gas-storing chamber 4, the gas calibration tube 6, and the communication tubes 7 and 8 connected thereto, a gas circulation unit 12 comprising a diaphragm pump is provided in the communication pipe 7. The gas circulation unit 12 is to circulate the gas components permeated from the insulating oil through the gas permeating material 3, where the gas in the gas-storing chamber 4 can be forced to circulate through the closed loop comprising the communication pipe 7, the gas calibration pipe 6 and the communication pipe 8.

The circulation passage is also provided with a valve 13 for bringing the subatmospheric pressure gas in the circulation passage into the normal pressure. The valve 13 is open to the gas-storing chamber 4 at one end, and to the atmosphere at the other end in the embodiment of FIG. 5.

Normally, the six-way switch valve 5 is kept in such a state that port 5F is communicated with port 5A, port 5B with port 5C and port 5D with port 5E, as shown by the full line in FIG. 5. When the insulating oil 2 in the transformer is a degasified insulating oil, a subatmospheric pressure prevails in the gas-storing chamber 4 and the gas calibration tube 6 connected thereto. Thus, the valve 13 is made open to the atmosphere to introduce air into the circulation passage before the detection of gas components, and to bring the gas-storing chamber 4 and the gas calibration tube 6 into the normal pressure. Then, the valve 13 is closed again. Since the air is introduced into the gas-storing chamber 4, the gas concentration is higher in the gas calibration tube 6 than in the gas-storing chamber 4. Thus, the gas circulation unit 12 is actuated to force the gas to circulate between the gas-storing chamber 4 and the gas calibration tube 6 to obtain a uniform mixture through stirring. After the stirring operation for a predetermined time, the gas circulation unit 12 is stopped, and communication state of the ports of six-way switch valve 5 are switched to that shown by dotted line in FIG. 5 to isolate the gas calibration tube 6 from the gas-storing chamber 4 and to connect it to the carrier gas inlet pipe 10 and discharge pipe 11. By the switching operation, the gas in the gas calibration tube 6 is pushed off from the gas calibration tube 6 by the carrier gas and led to the gas chromatographic device 9 for detection.

In such a structure as described above, the changes in peak output value under a subatmospheric pressure prevailing in the gas calibration tube 6 due to the use of degasified insulating oil 2 can be eliminated. That is, it is not necessary to provide a special pressure gage, etc. at the gas calibration tube 6 for gas pressure correction to gas concentration, and thus measuring operation is more simple in the present invention.

The valve 13, gas circulation unit 12 and six-way switch valve 5 can be interlocked and automated for a series of operations, and the present invention is not limited to manual operations.

In FIG. 5, the valve 13 is provided at the gas-storing chamber 4, but can be provided at any position between the six-way switch valve 5 and the gas-storing chamber 4. Thus, the valve 13 is not limited to the provision at the gas-storing chamber 4. Any valve can be used for the six-way switch valve 5 so long as it has the similar functioning.

As described above, the present invention can measure exact concentrations of permeated gas components by bringing the subatmospheric pressure in the gas calibration tube to the normal pressure before detection in a gas chromatographic device and by uniformly stirring the gas in the gas-storing chamber and the gas calibration tube.

What is claimed is:

1. A method for detecting gas components in the oil in an oil-filled device, which comprises separating gas components dissolved in an insulating oil in an oil-filled device through a gas-permeating material, storing the separated gas components in a gas calibration tube through a switch valve, and detecting the gas components stored in the gas calibration tube by a gas chromatographic device, wherein an improvement comprises pushing the gas components separated from the insulating oil and stored in the gas calibration tube in advance off from the gas calibration tube by a carrier gas, and mixing the gas components by stirring before the detection in the gas chromatographic device.

2. A method for detecting gas components in the oil in an oil-filled device, which comprises separating gas components dissolved in an insulating oil in an oil-filled device through a gas-permeating material, storing the separated gas components in a gas calibration tube through a switch valve, and detecting the gas components stored in the gas calibration tube by a gas chromatographic device, wherein an improvement comprises storing the gas components separated from the insulating oil in a gas-storing chamber, exposing the gas-storing chamber to the atmosphere, thereby bringing the gas-storing chamber into the normal pressure, circulating the gas under the normal pressure between the gas-storing chamber and the gas calibration tube, and then supplying the gas in the gas calibration tube to the gas chromatographic device.

3. The method according to claim 1 or 2, wherein the gas components stored in the gas-storing chamber is under a subatmospheric pressure.

4. An apparatus for detecting gas components in the oil in an oil-filled device, which comprises a gas-storing chamber being proviced at an oil-filled device containing an insulating oil through a gas-permeating material capable of separating gas components from the insulating oil, a gas calibration tube being proviced at the gas-storing chamber through a switch valve, and a gas chromatographic device connected to the gas calibration tube through the switch valve, wherein an improvement comprises at least one stirring mixer having at least one throttle perforation being provided in a carrier gas passage for supplying the gas components from the gas calibration tube to the gas chromatographic device at the upstream side of a gas separation column of the gas chromatographic device.

5. The apparatus according to claim 4, wherein the stirring mixture has a gas impingement plate at the downstream side of the throttle perforation.

6. An apparatus for detecting gas components in the oil in an oil-filled device, which comprises a gas-storing chamber being provided at an oil-filled device containing an insulating oil through a gas-permeating material capable of separating gas components from the insulating oil, a gas calibration tube being provided at the gas-storing chamber through a switch valve, and a gas chromatographic device connected to the gas calibration tube through the switch valve, wherein an improvement comprises a circulation passage being provided between the gas-storing chamber and the gas calibration tube, a valve capable of being exposed to the atmosphere being provided at the circulation passage, and a gas circulation unit being provided at the circulation passage for circulating the gas in the circulation passage.

* * * * *